(12) United States Patent
Chang

(10) Patent No.: US 9,901,698 B2
(45) Date of Patent: Feb. 27, 2018

(54) RESPIRATORY MASK

(71) Applicant: Hsiner Co., LTD., Taichung (TW)

(72) Inventor: Eric Chang, Taichung (TW)

(73) Assignee: HSINER CO., LTD., Taichung (TW)

(*) Notice: Subject to any disclaimer, the term of this patent is extended or adjusted under 35 U.S.C. 154(b) by 358 days.

(21) Appl. No.: 14/705,517

(22) Filed: May 6, 2015

(65) Prior Publication Data

US 2016/0121069 A1 May 5, 2016

(30) Foreign Application Priority Data

Nov. 3, 2014 (TW) .............................. 103138056 A

(51) Int. Cl.
*A61M 16/06* (2006.01)
*A61M 16/08* (2006.01)

(52) U.S. Cl.
CPC .... *A61M 16/0644* (2014.02); *A61M 16/0616* (2014.02); *A61M 16/0683* (2013.01); *A61M 16/0816* (2013.01)

(58) Field of Classification Search
CPC ....... A61M 16/0633; A61M 16/0644–16/0655
See application file for complete search history.

(56) References Cited

U.S. PATENT DOCUMENTS

| | | | | |
|---|---|---|---|---|
| 6,823,869 B2 * | 11/2004 | Raje | ...................... | A61M 16/06 128/206.24 |
| 7,640,933 B1 * | 1/2010 | Ho | ........................ | A61M 16/06 128/206.21 |
| 2003/0075182 A1 * | 4/2003 | Heidmann | ............ | A61M 16/06 128/207.11 |
| 2003/0221691 A1 * | 12/2003 | Biener | .................. | A61M 16/06 128/206.24 |
| 2004/0112387 A1 * | 6/2004 | Lang | ..................... | A61M 16/06 128/206.24 |
| 2005/0155603 A1 * | 7/2005 | Frerichs | ................ | A61M 16/06 128/206.21 |
| 2006/0076019 A1 * | 4/2006 | Ho | ........................ | A61M 16/06 128/206.24 |
| 2008/0066745 A1 * | 3/2008 | Janbakhsh | ............ | A61M 16/06 128/200.24 |

* cited by examiner

*Primary Examiner* — Valerie L Woodward
(74) *Attorney, Agent, or Firm* — Guice Patents PLLC

(57) ABSTRACT

A respiratory mask includes a mask body and an adjusting unit. The mask body has a frame portion, a flexible portion extending from the frame portion, and a forehead pad. The flexible portion has a mask-connecting end that is adjacent to the frame portion, and a pad-connecting end that is distal from the frame portion and connected to the forehead pad. The adjusting unit has a hardness greater than that of the flexible portion, and is removably coupled to the flexible portion for adjusting a curvature of the flexible portion and a distance between the forehead pad and the frame portion.

8 Claims, 7 Drawing Sheets

US 9,901,698 B2

RESPIRATORY MASK

CROSS-REFERENCE TO RELATED APPLICATION

This application claims priority of Taiwanese Application No. 103138056, filed on Nov. 3, 2014.

FIELD

The disclosure relates to a respiratory mask, and more particularly to a respiratory mask with a removable adjusting unit.

BACKGROUND

Referring to FIG. 1, a conventional respiratory mask 11 includes a mask unit 111 adapted to cover the mouth and nose of a user 12 and a rigid forehead supporting member 112 mounted to the mask unit 111 and adapted to abut against the forehead of the user 12. The mask unit 111 is adapted to be provided with a gas tube 13 for supplying the user 12 with positive pressure air therethrough.

When in use, two straps 14 are respectively connected to the forehead supporting member 112 and the mask unit 111. Each of the straps 14 extends from two opposite ends of a corresponding one of the forehead supporting member 112 and the mask unit 111 for surrounding the user's head. Thereby, the two opposite ends of the forehead supporting member 112 abut against the forehead of the user 12 and the two opposite ends of the mask unit 111 abut against the cheeks of the user 12 for covering his/her nose and mouth. However, the fittingness and closeness of the respiratory mask 11 on the user 12 depend largely upon the facial features of the user 12, such as face, forehead and nose shapes. In other words, the conventional respiratory mask 11 is unable to fit closely onto all faces and may result in the user's uncomfortableness or air leakage.

SUMMARY

Therefore, an object of the disclosure is to provide a respiratory mask that is adjustable to closely fit the facial features of a user.

According to the disclosure, a respiratory mask includes a mask body and an adjusting unit. The mask body has a frame portion, a flexible portion extending from the frame portion, and a forehead pad. The flexible portion has a mask-connecting end that is adjacent to the frame portion, and a pad-connecting end that is distal from the frame portion and connected to the forehead pad. The adjusting unit has a hardness greater than that of the flexible portion, and is removably coupled to the flexible portion for adjusting a curvature of the flexible portion and a distance between the forehead pad and the frame portion.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
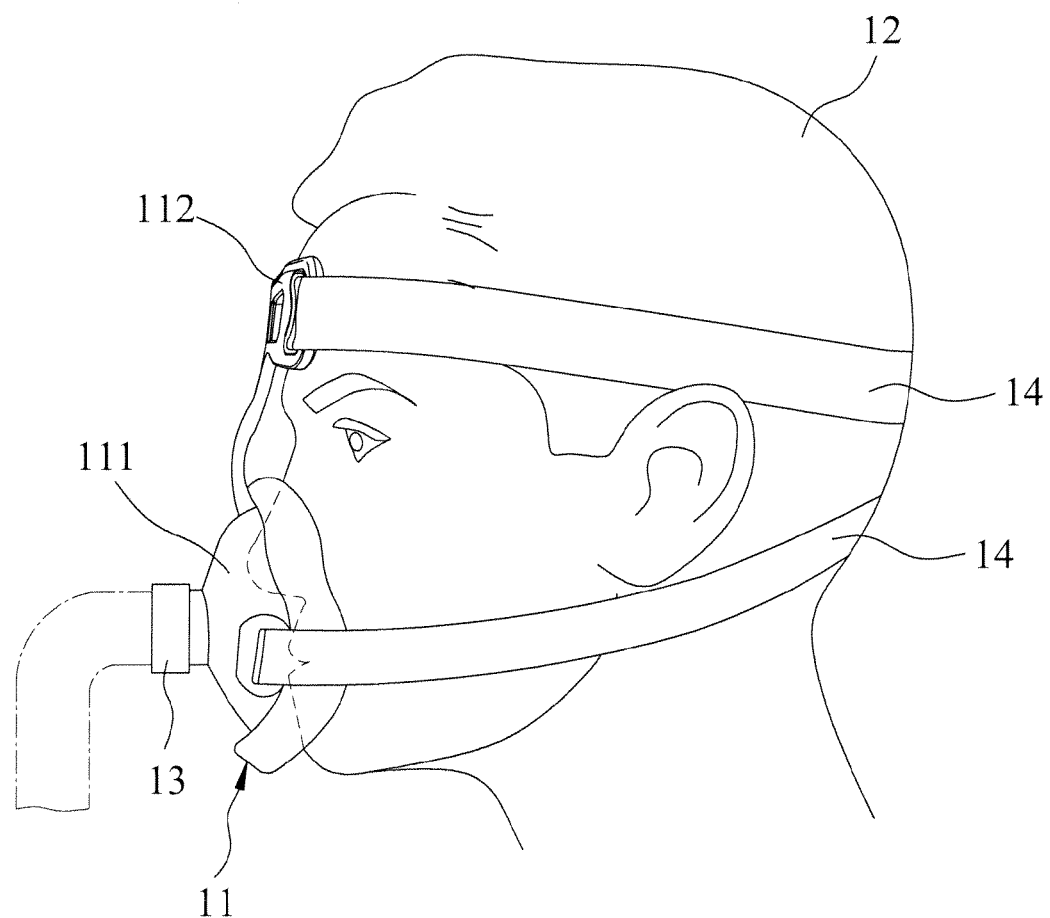
FIG. 1 is a side view illustrating a conventional respiratory mask in use.

Before the disclosure is described in greater detail, it should be noted that like elements are denoted by the same reference numerals throughout the disclosure.

Figure 2:
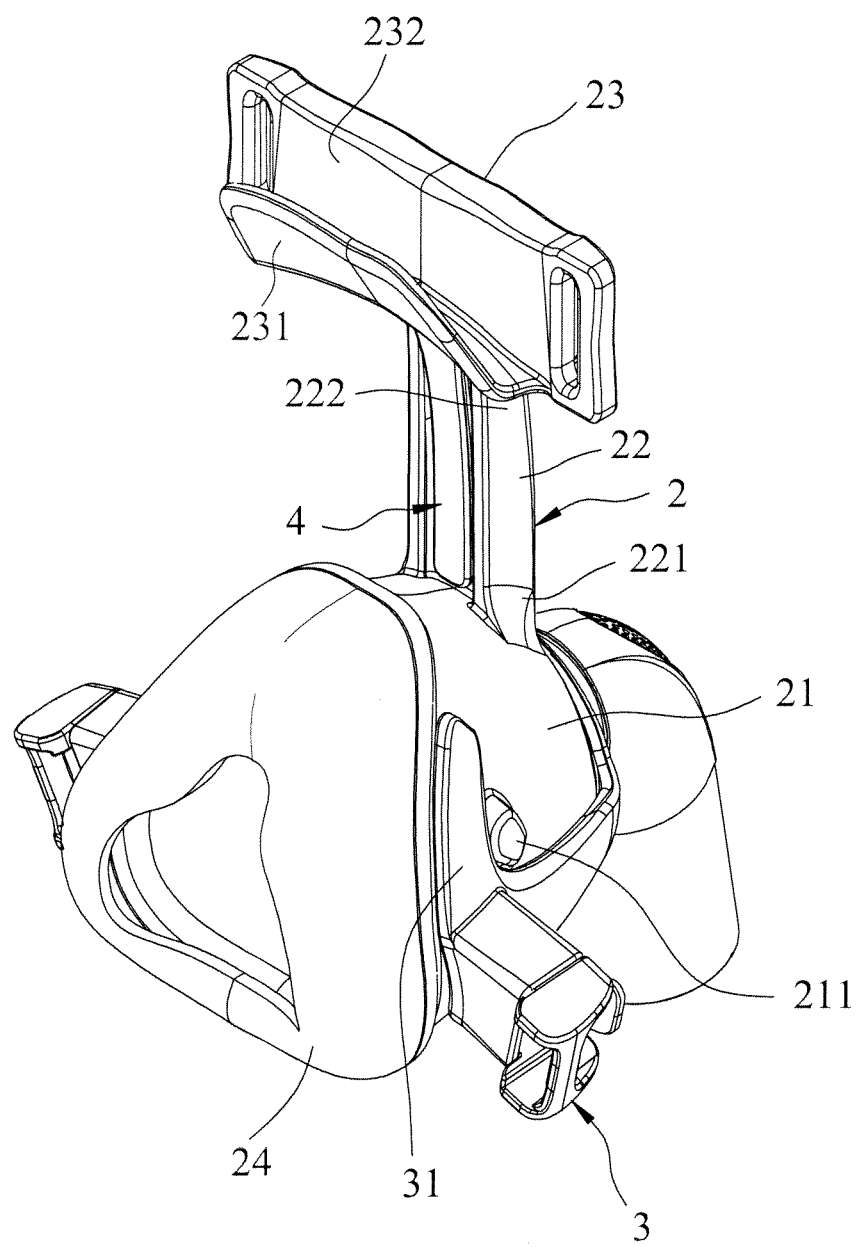
FIG. 2 is a perspective view illustrating a first embodiment of a respiratory mask according to the disclosure.
Figure 3:
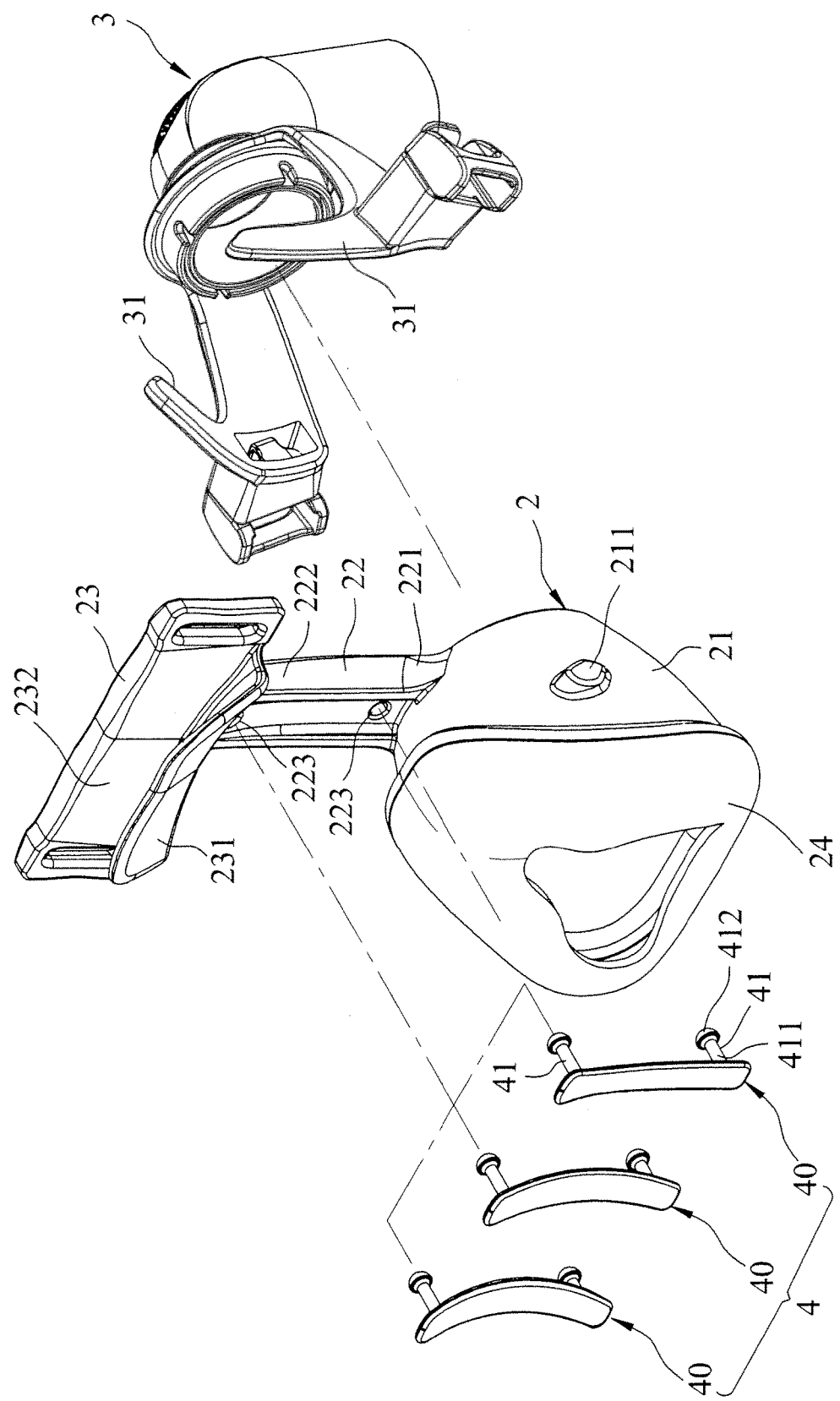
FIG. 3 is an exploded perspective view illustrating the first embodiment.

Referring to FIGS. 2 and 3, a first embodiment of a respiratory mask according to the disclosure is illustrated. In this embodiment, the respiratory mask includes a mask body 2, a tube connector 3 and an adjusting unit 4.

The mask body 2 has a frame portion 21, a flexible portion 22 extending from the frame portion 21, a forehead pad 23 connected to the flexible portion 22, and a face pad 24 that is connected to the frame portion 21 on a user-facing side of the mask body 2. In one design of this embodiment, the mask body 2 may be formed as one piece.

The frame portion 21 of the mask body 2 has two projections 211 on two opposite lateral sides thereof.

The flexible portion 22 of the mask body 2 has a mask-connecting end 221 that is adjacent to the frame portion 21, a pad-connecting end 222 that is distal from the frame portion 21 and connected to the forehead pad 23, and two positioning parts 223 that are spaced apart from each other. As a non-limiting example, the positioning parts 223 of the flexible portion 22 are formed as holes and are respectively adjacent to the mask-connecting end 221 and the pad-connecting end 222.

The forehead pad 23 of the mask body 2 has a main segment 232 connected to the pad-connecting end 222 of the flexible portion 22 and an abutting portion 231 that is inclined and extends from a bottom end of the main segment 232 away from the flexible portion 22.

The tube connector 3 includes two hooks 31 that respectively and removably engage the projections 211 to connect the tube connector 3 and the mask body 2.

The adjusting unit 40 has a hardness greater than that of the flexible portion 22 and is removably coupled to the flexible portion 22 for adjusting a curvature of the flexible portion 22 and a distance between the forehead pad 23 and the frame portion 21.

The adjusting unit 4 includes at least one adjusting member 40 that has two engaging parts 41 that engage removably and respectively the positioning parts 223 of the mask body 2. In this embodiment, the adjusting unit 40 includes three adjusting members 4 with different curvatures.

Each of the engaging parts 41 of each of the adjusting members 40 has a rod segment 411, and a bead segment 412 that is connected to a distal end of the rod segment 411 and that engages removably a respective one of the positioning parts 223.

Figure 4:
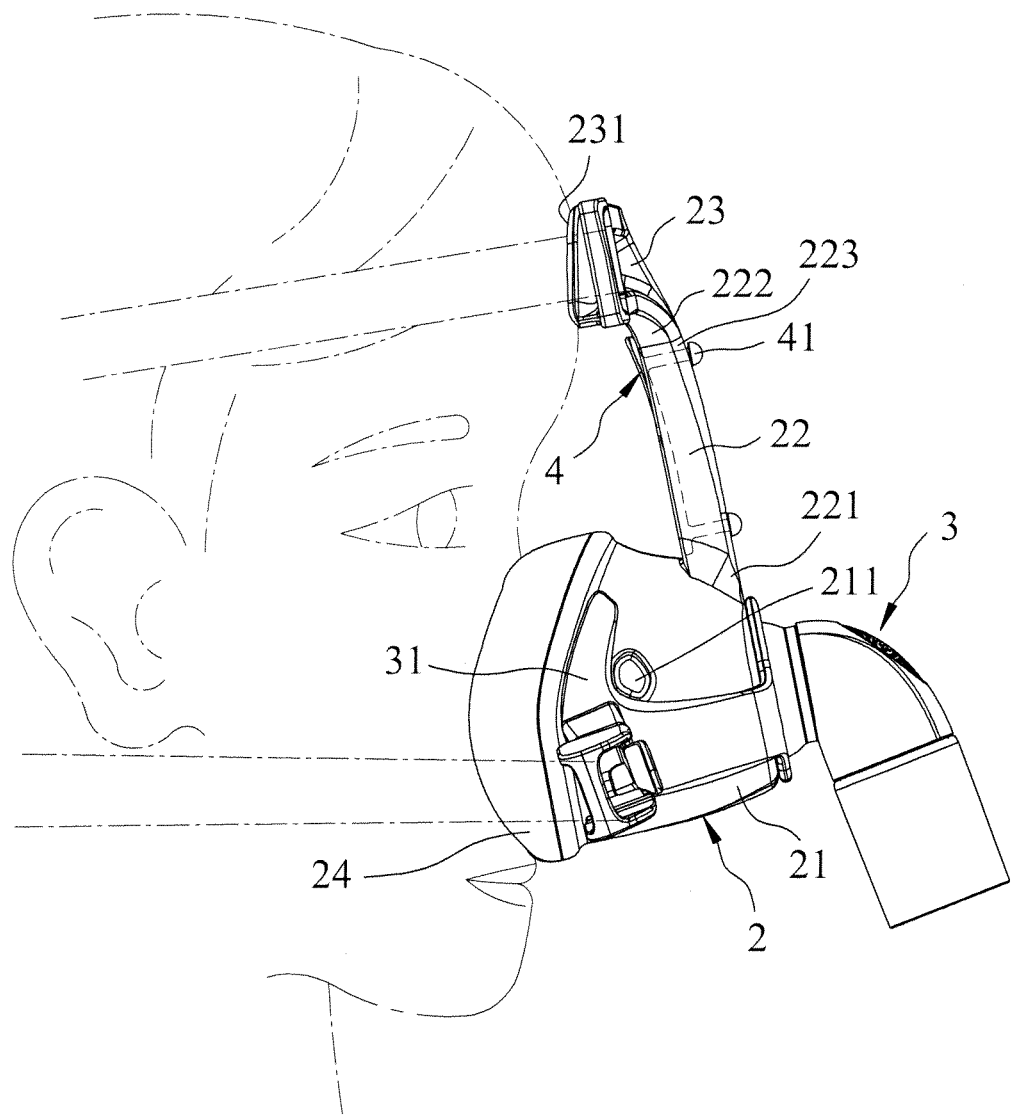
FIG. 4 is a side view illustrating the first embodiment in use by a user.

Referring to FIG. 4, the first embodiment of the respiratory mask according to the disclosure when applied on a user with a relatively full forehead is illustrated. In this configuration, one of the adjusting members 40 with a smaller curvature is selected to be engaged with the flexible portion 22 in such a manner that the curvature of the flexible portion 22 is adjusted and maintained, the face pad 24 of the mask body 2 abuts against and covers the nose and mouth of the user, and the forehead pad 23 abuts against the forehead of the user.

Figure 5:
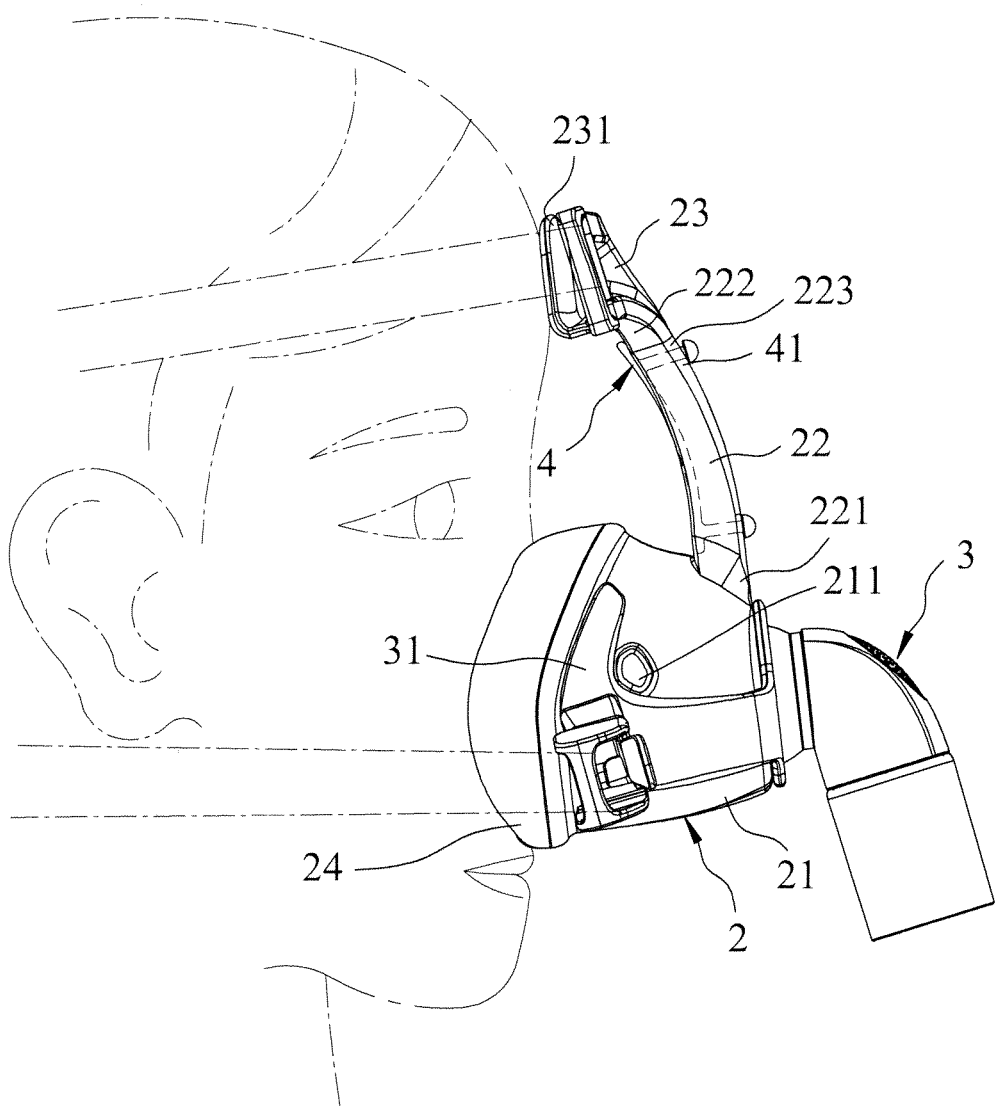
FIG. 5 is a side view illustrating the first embodiment in use by another user.

Referring to FIG. 5, the first embodiment of the respiratory mask according to the disclosure, when applied on a user with a relatively flat forehead is illustrated. In this configuration, one of the adjusting members 40 with a greater curvature is selected to be engaged with the flexible portion 22 so as to closely fit the respiratory mask onto the face of the user.

Figure 6:
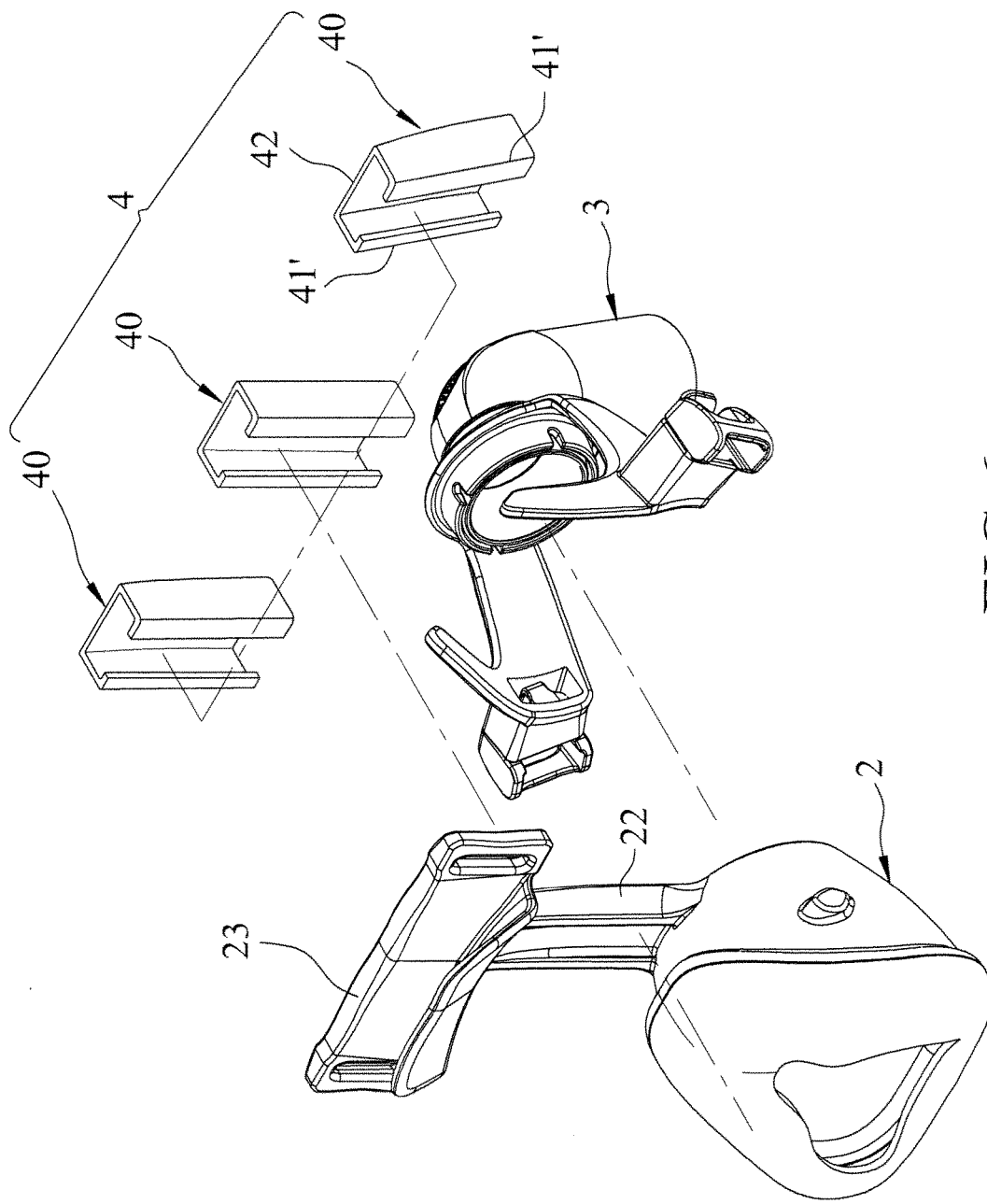
FIG. 6 is an exploded perspective view illustrating a second embodiment of the respiratory mask according to the disclosure.
Figure 7:
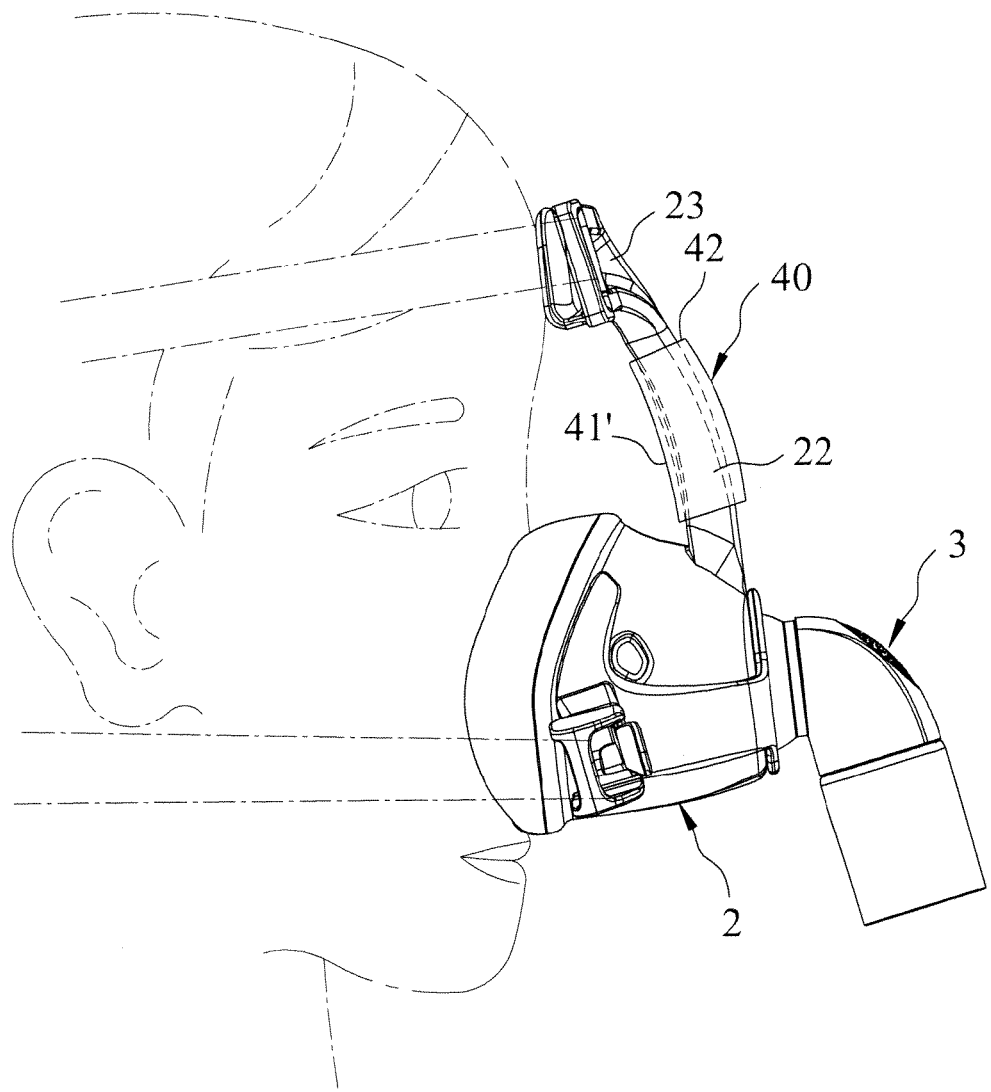
FIG. 7 is a side view illustrating the second embodiment in use.

Referring to FIGS. 6 and 7, a second embodiment of the respiratory mask according to the disclosure is illustrated. The second embodiment has a structure similar to that of the first embodiment. However, each of the adjusting members 40 has a U-shaped body 42 and the engaging parts 41' are formed as two flanges extending from two arms of the U-shaped body 42, and no holes 223 are formed in the flexible portion 22. One of the adjusting members 40 with a proper curvature clamps removably on the flexible portion 22 in a manner that the flexible portion 22 is fitted in the groove of the U-shaped body 42.

In view of the foregoing, since the tube connector 3 and the adjusting members 40 are removably coupled to or engaged with the mask body 2, the mask body 2 is easily replaceable with a new one after long-term use. Additionally, since the hardness of the adjusting members 40 is greater than that of the flexible portion 22, deformation of the flexible portion 22 is alleviated.

Moreover, since the mask body 2 may be formed as one piece, the respiratory mask according to the disclosure is lightweight and able to be easily assembled. By virtue of the adjusting members 40 with different curvatures, the respiratory mask can fit onto users with different facial features so that air leakage may be prevented and comfort is enhanced.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A respiratory mask comprising:
a mask body that has a frame portion, a flexible portion extending from said frame portion and having a mask-connecting end that is adjacent to said frame portion, and a pad-connecting end that is distal from said frame portion, and a forehead pad connected to said pad-connecting end; and
an adjusting unit that has a hardness greater than that of said flexible portion, and that is removably coupled to said flexible portion for adjusting a curvature of said flexible portion and a distance between said forehead pad and said frame portion;
wherein: said flexible portion further has two positioning parts that are spaced apart from each other; and said adjusting unit includes at least one adjusting member that has two engaging parts that engage removably and respectively said positioning parts;
wherein said engaging parts of said at least one adjusting member clamps removably on said positioning parts of said flexible portion;
wherein said adjusting unit includes a plurality of said adjusting members with different curvatures.

2. The respiratory mask as claimed in claim 1, wherein said forehead pad of said mask body has a main segment connected to said pad-connecting end of said flexible portion, and an abutting portion being inclined and extending from a bottom end of said main segment away from said flexible portion.

3. The respiratory mask as claimed in claim 2, wherein: said frame portion of said mask body has two projections on two opposite lateral sides thereof; and said respiratory mask further comprises a tube connector including two hooks that respectively and removably engage said projections to connect said tube connector and said mask body.

4. The respiratory mask as claimed in claim 3, wherein said mask body further has a face pad connected to said frame portion.

5. A respiratory mask comprising:
a mask body that has a frame portion, a flexible portion extending from said frame portion and having a mask-connecting end that is adjacent to said frame portion, and a pad-connecting end that is distal from said frame portion, and a forehead pad connected to said pad-connecting end; and
an adjusting unit that has a hardness greater than that of said flexible portion, and that is removably coupled to said flexible portion for adjusting a curvature of said flexible portion and a distance between said forehead pad and said frame portion;
wherein: said flexible portion further has two positioning parts that are spaced apart from each other; and said adjusting unit includes at least one adjusting member that has two engaging parts that engage removably and respectively said positioning parts;
wherein said positioning parts of said flexible portion are respectively adjacent to said mask-connecting end and said pad-connecting end;
wherein: each of said positioning parts of said flexible portion is formed as a hole; and each of said engaging parts of said at least one adjusting member has a rod segment and a bead segment that is connected to a distal end of said rod segment, and engages removably a respective one of said positioning parts;
wherein said adjusting unit includes a plurality of said adjusting members with different curvatures.

6. The respiratory mask as claimed in claim 5, wherein said forehead pad of said mask body has a main segment connected to said pad-connecting end of said flexible portion, and an abutting portion being inclined and extending from a bottom end of said main segment away from said flexible portion.

7. The respiratory mask as claimed in claim 6, wherein: said frame portion of said mask body has two projections on two opposite lateral sides thereof; and said respiratory mask further comprises a tube connector including two hooks that respectively and removably engage said projections to connect said tube connector and said mask body.

8. The respiratory mask as claimed in claim 7, wherein said mask body further has a face pad connected to said frame portion.

* * * * *